United States Patent [19]

Flemer, III

[11] Plant 4,119

[45] Oct. 4, 1977

[54] **VINE — *CAMPSIS RADICANS***

[75] Inventor: William Flemer, III, Princeton, N.J.

[73] Assignee: Treesearch

[21] Appl. No.: 732,492

[22] Filed: Oct. 14, 1976

[51] Int. Cl.[2] ..... A01H 5/00

[52] U.S. Cl. ..... Plt./54

[58] Field of Search ..... Plt./54

*Primary Examiner*—Robert E. Bagwill

*Attorney, Agent, or Firm*—Frank B. Robb

[57] ABSTRACT

This invention relates to a novel variety of *Campsis radicans,* characterized by its dark red blossoms and glossy foliage.

1 Drawing Figure

The present invention relates to a new and distinct variety of Vine known as *Campsis radicans* that I have designated "Crimson Trumpet" and which was originated by me in nursery property owned by Princeton Nurseries, Plainsboro Township, N.J.

I had been growing a number of vines in a row of *Campsis radicans* which were originally started from local seed plants and were being cared for and growing in cultivated condition, when I was able to notice a substantial difference in a certain vine by reason of the flowers thereof, which were a most distinctive and noticeable dark, rich red color, thereby standing out from the normal orange color of the flowers in this particular row of *Campsis radicans.*

Upon closer inspection, I determined that there was a single plant in a group of plants in this particular row, and I therefore carefully preserved the seedling, and after a series of propagations by soft wood stem cuttings performed in the nursery aforesaid in the usual manner, I found that the dark, rich red color of the flowers proved to be fixed and fully established, compared with the regular seedlings in the row and/or other rows in which they had been growing.

Further tests and observations conducted by me showed that the new seedlings propagated by soft wood stem cuttings, continued to produce the rich, dark red color of the flowers, and further it was noticed that the leaves have a decidedly glossy upper surface in contrast to the normal dull upper surface of usual *Campsis radicans* leaves.

As before stated, subsequently propagated plants of this particular clone grown from the cuttings referred to, have maintained the dark color of the flowers and the glossy upper surface of the leaves.

With the foregoing in mind, therefore, I am convinced that my new seedling, *Campsis radicans,* is in fact one which will prove popular if for no other reason than the principal characteristics which are as follows:

1. The dark, rich red color of the flowers;
2. The glossy upper surface of the leaves compared to the dull upper surface of ordinary *Campsis radicans* leaves;
3. The ability to propagate by soft wood stem cuttings very quickly; and
4. The typical abundant quantity of blooms borne in terminal cymes.

The accompanying drawing shows a typical vine of my new variety in close-up view particularly of the flowers thereon, illustrating the dark, rich red color thereof, the outstanding characteristic, with indication of the smooth glossy upper surface of the leaves of my new variety.

The following is a detailed description of my new variety of the vine *Campsis radicans,* with color terminology in accordance with the Munsell Color Chart, except where general color terms of ordinary dictionary significance are appropriate, and adequate for understanding, as based on observations made from specimen plants grown in the nursery on the property owned by Princeton Nurseries in Plainsboro Township, N.J.

Parentage: A newly found seedling in a row of the vine *Campsis radicans.*

Propagation: Holds its distinctive characteristics through succeeding propagations by soft wood stem cuttings.

Vine: Large; climbing by aerial rootlets; tall — ultimate height 20 to 25 ft., hardy;

Trunk: On old vines. Slender and rough.

Branches: Slender — smooth.

*Color.*—Munsell Color Chart — Moderate Reddish Brown 2.5 Y.R. 3/3.

*Lenticels.*—Number — not abundant.

Leaves:

*Quantity.*—Moderately abundant, pinnate, opposite, 11 to 13 leaflets.

*Length.*—30 to 35 cm. Width — 12 to 14 cm.

*Shape.*—Pinnate — Leaflets 7 cm. long, 3.5 cm. wide.

*Color.*—Upper surface — Glossy, Moderate Olive Green 7.5 G.Y. 4/4. Under surface — Moderate Yellow Green 7.5 G.Y. 5/7.

*Thickness.*—Medium.

*Margin of leaflet.*—Serrate.

*Petiole.*—Long — usually 6 to 7 cm. long.

*Glands.*—Not conspicuous.

*Stipules.*—None.

Flower buds: Flowers borne on current season's growth.

Flowers: Born in terminal cymes.

*Dates of first blooming.*—July 5-6; Full Bloom: August 1-30 in New Jersey.

*Quantity.*—Abundant.

*Size.*—Medium 7 to 8 cm long, 4.5 cm. wide.

Petalage: Calyx tubular campanulate, 5 lobed, corolla funnel shaped.

*Number of lobes.*—5.

*Shape of lobes.*—Rounded.

*Size of individual lobes.*—Length 2 cm. Width 2.2 cm.

*Color of flowers.*—Dark Red 5 R 3/7.

Fruits:

*When borne.*—Fall.

*Abundance.*—Not abundant.

*Size.*—Long pod 12-16 cm. long having many winged seeds.

*Color.*—Light Brown.

I claim:

1. A new and distinct variety of *Campsis radicans,* substantially as herein shown and described, characterized particularly as to novelty by the dark, rich red color of the flowers in contrast to the normal orange color of *Campsis radicans* flowers, and the glossy upper surface of the leaves in contrast to the normal dull upper surface of usual *Campsis radicans* leaves.

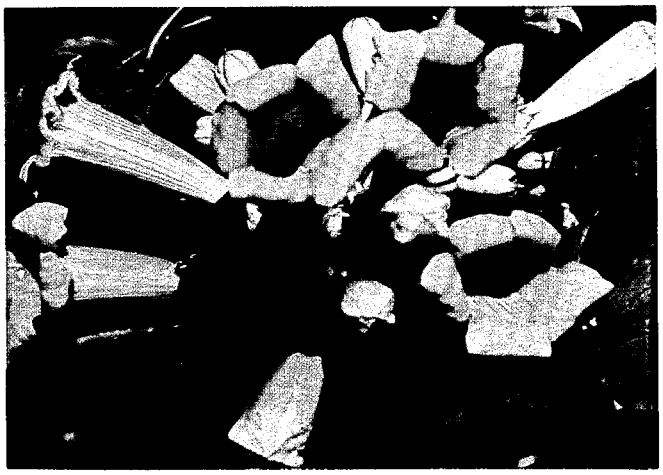

* * * * *